United States Patent [19]
McEleney et al.

[11] Patent Number: 5,955,062
[45] Date of Patent: Sep. 21, 1999

[54] COLORED FORMULATIONS FOR APPLICATION TO HUMAN SKIN

[75] Inventors: John McEleney, Newton; Wende Reenstra, Boston; Curtis A. Vock, Salem, all of Mass.

[73] Assignee: SeeUV, Charlestown, Mass.

[21] Appl. No.: 09/024,458

[22] Filed: Feb. 17, 1998

Related U.S. Application Data

[63] Continuation of application No. 08/895,962, Jul. 17, 1997, Pat. No. 5,753,210, which is a continuation of application No. 08/688,694, Jul. 25, 1996, Pat. No. 5,680,962, and application No. 08/340,540, Nov. 16, 1994, Pat. No. 5,567,420.

[51] Int. Cl.$^6$ .............................. A61K 7/42; A61K 7/44; A61K 7/00
[52] U.S. Cl. ........................... 424/59; 424/60; 424/78.02; 424/78.03; 424/400; 424/401; 514/844; 514/846; 514/847; 514/937; 514/938; 514/939; 514/946; 514/947
[58] Field of Search ........................... 424/59, 60, 78.02, 424/78.03, 400, 401; 514/844, 846, 847, 937, 938, 939, 946, 947

[56] References Cited

U.S. PATENT DOCUMENTS

| | | | |
|---|---|---|---|
| 2,366,759 | 1/1945 | Thomas et al. | 167/85 |
| 2,496,270 | 2/1950 | Coler | 167/22 |
| 3,031,104 | 4/1962 | Moskovitz | 222/94 |
| 3,042,263 | 7/1962 | Gallo, Sr. | 222/94 X |
| 3,152,731 | 10/1964 | Prussack | 222/94 X |
| 3,182,860 | 5/1965 | Gallo, Sr. | 222/94 |
| 3,468,458 | 9/1969 | Leigh | 222/94 |
| 3,751,563 | 8/1973 | Richardson | 424/60 |
| 3,814,287 | 6/1974 | Darbon et al. | 222/94 |
| 4,084,983 | 4/1978 | Bernhard et al. | 16/289 |
| 4,271,984 | 6/1981 | Ducros et al. | 222/94 |
| 4,954,544 | 9/1990 | Chandaria | 524/111 |
| 5,426,210 | 6/1995 | Kato et al. | 560/55 |
| 5,523,075 | 6/1996 | Fuerst et al. | 424/59 |
| 5,567,420 | 10/1996 | McEleney et al. | 424/60 |
| 5,609,852 | 3/1997 | Galley | 424/59 |
| 5,753,210 | 5/1998 | McEleney et al. | 424/59 |

*Primary Examiner*—Shelley A. Dodson
*Attorney, Agent, or Firm*—Duft, Graziano & Forest, P.C.; Curtis A. Vock

[57] ABSTRACT

A lotion such as a sunscreen includes a pH indicator which colorizes the lotion until the lotion is applied to the human skin, whereinafter the colored lotion turns clear. A physiologically compatible pH indicator such as phenolphthalein is used which has a red appearance from pH 7.5+ and which has a clear appearance from about pH 7.0 to 7.5, the general pH range of the skin. The invention is suitable for use in any lotion, gel, mousse or medication that is best applied in an even and uniform manner to the skin. Accordingly, one preferred use of the invention is in UV-protecting sunscreens so that a user can ensure even distribution of the sunscreen on the body. In certain aspects of the invention, a cap houses the pH indicator and attaches to a container of the lotion, e.g., a sunscreen. The pH indicator mixes with the lotion as it is applied to the skin. The invention further provides methods of manufacturing sunscreens and the like with a pH indicator that turns substantially colorless upon prolonged contact with the skin.

24 Claims, 5 Drawing Sheets

COLORED FORMULATIONS FOR APPLICATION TO HUMAN SKIN

CROSS-REFERENCE TO RELATED APPLICATION

This is a continuing application of commonly-owned and patent application Ser. No. 08/895,962, filed on Jul. 17, 1997, now U.S. Pat. No. 5,753,210 which is a continuing application of prior application Ser. No. 08/688,694, filed on Jul. 25, 1996 (now U.S. Pat. No. 5,680,962, issued on Oct. 28, 1997) and of Ser. No. 08/340,540, filed on Nov. 16, 1994 (now U.S. Pat. No. 5,567,420, issued Oct. 22, 1996), each of which are hereby incorporated by reference.

BACKGROUND OF THE INVENTION

Darker skin pigmentation is considered desirable by many persons, socially and aesthetically. At present, the most common method for darkening the skin is through sun-tanning, using either natural sunlight or specially designed ultraviolet (UV) light sources, e.g., taning lamps.

However, extended exposure of human skin to ultraviolet light is known to have adverse consequences, both in the short term and in the long term. Specifically, in the short term, individuals exposed to UV risk a painful sunburn and keratitis. In the long term, extended exposure to ultraviolet radiation can result in photo-aging and "leathery" skin, and can further result in various forms of skin cancer and ultimately death.

Fair-skinned individuals are particularly susceptible to sun-induced skin disorders and cancers. For example, they face a higher risk of melanoma (skin cancer), and often incur photo-aging or dermatoheliosis, a condition characterized by wrinkling, irregular pigmentation, and surface roughness. However, even darker skinned individuals exposed to prolonged sunlight incur a high risk of skin cancer and exacerbated aging.

These risks, together with the continued desirability of the suntan look, have resulted in a wide range of UV protection suncreen agents. Such sunscreen agents are typically suspended in a cream, lotion, gel, mousses, waxed based sticks, aerosols, and alcohol sticks for topical application to the skin. For example, the Coppertone™ Company makes a large assortment of popular sunscreen lotions with varying degrees of sun block which extend the body's normal resistance to UV radiation.

One important step in the proper application of an UV protective suncreen lotion on the body is the even and complete coverage of all bodily areas which are exposed to the sun. Typical suncreen lotions and the like are applied as clear or white creams that are difficult to see upon application. It is thus difficult for a user of these typical suncreen lotions to assure even and complete coverage on the body. Consequently, it is common to miss spots, resulting in an uneven tan or burn, and the increased susceptibility to the several risks discussed above.

It is, accordingly, an object of the invention to provide a sunscreen agent which increases the likelihood of even and complete coverage when applied to the body.

Another object of the invention is to provide a UV protective suncreen lotion which reduces the risks associated with improper application to the body.

Still another object of the invention is to provide improvements to lotions, gels, mousses and creams that are applied topically to the human skin.

These and other objects of the invention will become apparent in the description which follows.

SUMMARY OF THE INVENTION

As used herein, "color indicator," "indicator," or "CI," includes the naturally occurring and synthetic derivatives of pH indicators. A "pH indicator" is a compound that changes its visible color upon a change in pH (hydrogen ion concentrations). Suitable pH indicators according to the invention include those indicators which are clear or colorless in the pH range of approximately 6.5–8.0, and which are colored or visible above or below that pH range.

The present invention includes a method for applying and distributing sunscreens and lotions evenly. In one aspect of the invention, a color indicator is added to such sunscreens or lotions for visual detection by a user of the sunscreen or lotion. The CI in the sunscreen or lotion composition initially has a visible color upon application to the skin, and changes or becomes clear (colorless) after a short time period (i.e., between about 0.5 and 10 minutes), thereby permitting the normal or unimpeded use of the product for its intended function (i.e., after the short time period, the user is not colored by the CI but rather has a skin color appearance that normally results from application of an uncolored lotion or sunscreen). The presence of the visible color on the epidermis is indicative of the location and amount of composition thereon, thereby enabling total coverage with, and even distribution of, the composition. In one aspect of the invention, such an even distribution of sunscreen ointment results in uniform protection from exposure to UV radiation.

The invention is next described further in connection with preferred embodiments, and it will be apparent that various additions, subtractions, and modifications can be made by those skilled in the art without departing from the scope of the invention.

BRIEF DESCRIPTION OF THE FIGURES

The present invention may be more easily and completely understood when taken in conjunction with the accompanying drawings, in which.

DETAILED DESCRIPTION OF ILLUSTRATED EMBODIMENTS

Figure 1:
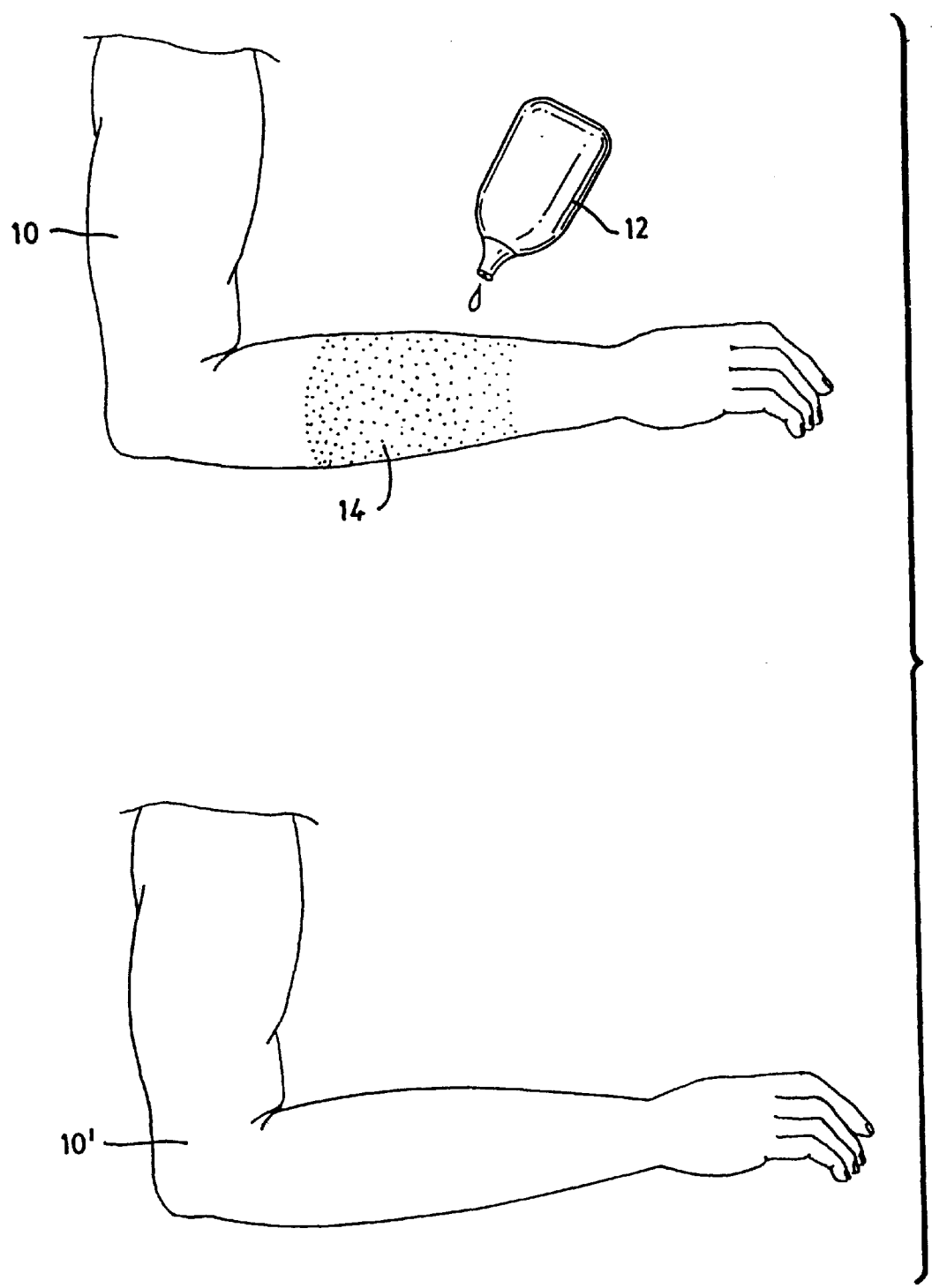
FIG. 1 illustrates a typical use of the invention.

The present invention provides compositions for application to the skin, including a pH indicator and methods of their preparation, as well as apparatus for temporarily colorizing the epidermis. The CI suitable for use in the invention are those CIs which are physiologically compatible with the skin, and which readily dissolve in creams and lotions. The CIs may be used individually or in combination. Suitable CIs are also those physiologically acceptable substances which appear clear at a pH of between approximately 6.5 and 8.0, and which appear colored at a pH outside this range. Suitable CIs also include those substances listed in Table 1 hereto.

The invention utilizes the fact that the pH of normal human skin is between approximately 7.0 and 7.5 at any given time. Therefore, one CI according to the invention has (i) dear appearance at a pH in the normal skin range of 7.0 to 7.5 and (ii) a colored appearance at a pH outside this range. Typical sunscreen creams and sun lotions have a pH of 7.5 or above. Thus, if a a is chosen which is red at pH 8.0, and that CI is added to a lotion with a pH of 8.0, then the lotion will appear red. When applied to the skin, however, the skin's pH will shift the overall lotion pH from 8.0 to 7.0–7.2, and will thus change the CI from red to colorless.

Alternatively, a sunscreen or lotion according to the invention is one which (i) has a pH of approximately 6.5 (or less) and (ii) utilizes a CI which is colored at pH 6.5 (or less) and colorless at pH 7.0 to 7.5. Consequently, upon application to human skin, the initially colored sunscreen or lotion pH will shift upwards, due to the skin's pH, to approximately pH 7.0 to 7.5, and will thus become colorless at that time.

Indicators according to the invention can be added during the manufacture or the formulation of the lotion, such as described below. Alternatively, by controlling the pH of the lotion, the CIs can also be added after formulation.

As described above, suitable indicators according to the invention are those which undergo a color change from colored to clear (i.e., substantially colorless) at a pH range of 6.5–8.0, and which are suitable for application to the human skin. Suitable indicators, for example, include phenolphthalein, esolphthalein, thymolphthalein, quinazolinedione, and ethyl-bis ethanoate. A color indicator such as phenolpthalein, for example, changes color from visible to clear when its pH changes from a pH that is higher or lower than 7.0–7.4 to a pH of 7.0–7.4. Other indicators according to the invention, such as Coumarin, and dioxyxanthone, respond to pH changes by changing from a fluorescent color to clear. A more comprehensive description of the indicators according to the invention is provided below in Table 1.

In accord with one embodiment of the invention, CIs are employed topically. For topcial use, it is desirable that a CI is dispersed in an emulsion of sunscreen or lotion and applied to the skin. For this purpose, the CIs are intended to be admixed in a pharmacologically acceptable topical carrier such as a gel, an ointment, a lotion, or a cream. Such carriers include, but are not limited to, water, glycerol, alcohol, propylene glycol, fatty alcohols, triglycerides, fatty acid esters, and mineral oils.

Sunscreening agents according to the invention include the UVA-type (typical UVA-type sunscreening agents include certain benzophenones and dibenzoyl methanes), the UVB type (typical UVB type sunscreening agents include substituted para-aminobenzoates, alkyl esters of para-methoxycinnamate and certain esters of salicylic acid), or a combination of the two. Generally, the sunscreening agents are used in amounts effective to provide the desired level of protection against UVA and/or UVB radiation. For example, the sunscreening agents are generally used in the amounts of about 2% to about 20% by weight of the total composition, with about 5% to about 18% being preferred, and about 2% to about 15% being most preferred.

Representative UVB-type sunscreening agents suitable for use with the invention include, without limitation, the following:

(A) DEA methoxyinnamate (diethanolamine salt of p-methoxy hydro cinnamate), e.g., tradename BERNEL HYDRO from Bernel Chemical Co., Inc.

(B) ethyl dihydroxypropl PABA (ethyl dihydroxypropyl p-aminobenzoate), e.g., tradename AMERSCREEN R from Amerchol Corp.;

(C) glycerol PABA (glyceryl-p-aminobenzoate), e.g., tradename NIPA G.M.P.A from NIPA Laboratories Inc.;

(D) homosalate (Homomenthyl salicylate), e.g., tradename KEMESTER HMS from Humko Chemical;

(E) octocrylene (2-ethylhexyl-2-cyano-3,3-diphenylacrylate), e.g., tradename UVNUL N-539 from BASF Chemical Co.;

(F) octyl dimethyl PABA (OCtyl dimethyl p-aminobenzoate, 2-ethylhexyl p-dimethylaminobenzoate, Padimate O), e.g., tradenames AMERSCOL, ARLATONE UVB, and ESCALOL 507 from Amerchol Corp., ICI Americas, Inc., and Van Dyk, respectively;

(G) octyl methoxycinnamate (2etylhexyl-p-methoxycinnamate), e.g., tradename PARSO_MCX from Bernel Chemical Co., Inc., or Givauden Corp.;

(H) octyl salicylate (2-ethylhexy salicylate), e.g., tradename SUNAROME WMO from Felton Worldwide, Inc.;

(I) PABA (p-amino benzoic acid), e.g., tradename PABA from EM Industries, Inc. and National Starch & Chemical Corp., and tradename NIPA PABA from NIPA Laboratories Inc.;

(J) 2-phenyl-benzimidazole-5-sulphonic acid (Novantisol), e.g., tradename EUSOLEX 232 and NEO-HEUOPAN HYDRO from EM Industries, Inc. and Haarmann & Reimer Corp., respectively;

(K) TEA salicylate (triethanolamine salicylate), e.g., tradenames SUNADROME W and SUNDROME G from Felton Worldwide, Inc.;

(L) 3(4-methylbenzlidene)camphor or 3(4-methylbenzylidene)boran-2-one, e.g., tradename EUSOLEX 6300 from EM Industries, Inc.; and (M) etocrylene (2-ethyl-2-cyano-3,3"-diphenylacrylate), e.g., tradename UVINUL N-35 from BASF Chemical Co.

Representative UVA type suncreening agents suitable for use with the invention include, without limitation, the following:

(A) benzophenone-3 (2-hydroxy-4-methoxy-benzophenone), e.g., tradename SPECTRA-SORB UV-9 and UVINUL M-40 from American Cyanamid Co. and BASF Chemical Co.,respectively;

(B) benzophenone-4 (sulisobenzone), e.g., tradename UV MS-40 from BASF Chemical Co.;

(C) benzophenone-8 (dioybenzone), e.g., tradename SPECTRA-SORB UV-24 from American Cyanamid Co.;

(D) methyl anthranilate (methyl-O-aminobenzoate), e.g., tradename SUNAROME UVA from Felton Worldwide, Inc.;

(E) benzophenone-1 (2,4,-dihydroxybenzophenone), e.g., tradename UVINUL 400 and UVASORB 20H from BASF Chemical Co. and TRI-K Industries, Inc., respectively;

(F) benzophenone-2 (2,2',4,4'-tetrahydroxy-benzohpenone), e.g., tradename UVINUL D-50 from BASF Chemical Co.;

(G) benzophenone-6 (2,2'-dihydroxy4,4'-dimethoxy-benzophenone0, e.g., tradename UVINUL D49 from BASF Chemical Co.;

(H) benzophenone-12 (octabenzone), e.g., tradename UVINOL 408 from BASF Chemical Co.;

(I) 4isopropyl dibenzoyl methane (1-pcumenyl-3-phenylpropane-1,3dione), e.g. tradename EUSOLEX 8020 from EM Industries Inc.; and (J) butyl methyl dibenzoyl methane (4-t-butyl-4'-methoxydibenzoyl methane), e.g. tradename PARSOL 1789 from Givaudan Corporation.

Physical sunscreening agents may also be added to the composition according to the invention. For example, red petrolatum in amounts of about 30% to about 99% by weight of the total composition, or titanium dioxide in amounts of about 2% to about 25% by weight of the total composition can be used. Talc, kaolin, chalk, and precipitated silica can also be used in effective amounts, e.g., about 1% to about 10% by weight of the total composition.

Additional sunscreening agents according to the invention include lawsone hydroxynaphthoquinone, $C_{10}H_6O_3$ (the coloring matter of henna leaves) with dihydroxy acetone.

In accord with preferred embodiments of the invention, at least one UVA-type or UVB-type sunscreening agent is preferably used in compositions designed to inhibit UV radiation. For example, the following UVB-type sunscreening agents can be used according to the invention: from about 1.5% to about 8.0% by weight of the total composition of octyl dimethyl PABA; octyl para- methoxycinnamate in amounts of about 1.5% to about 7.5% by weight of the total composition; homomethyl salicylate in amounts of about 4.0% to about 15% by weight of the total composition; and octyl salicylate in amounts of about 3% to about 5% by weight of the total composition.

In another embodiment, at least one of the following UVA type sunscreening agents can be added: benzophenone-3 in amounts of about 0.5% to about 6% by weight of the total composition; benzophenone-8 in amounts of about 0.5% to about 3% by weight of the total composition; and menthyl anthanilate in amounts of about 3.5% to about 5.0% by weight of the total composition.

The color indicator compositions according to the invention can be incorporated into formulations such as lotions, creams, gels, mousses, waxed based sticks, aerosols, alcohol sucks and the like. These formulations are well known in the art. For example, information regarding such formulations may be found in (i) Balsam, M. S., and Sagrin, E. (Editors) *Cosmetics Science and Technology,* Second Edition, Volumes 1 and 2, Wiley-Interscience, a division of John Wiley & Sons, Inc., New York, copyright 1972; and (ii) Flick, E. W., *Cosmetic and Toiletry Formulations,* Noyes Publications, 1984, each of which is incorporated herein by reference.

In addition to the UV-blocking additives described above, lotions and/or sunscreens according to the invention can include other compounds, including any of the following: (i) emollients, (ii) emulsifiers, (iii) surfactants, (iv) waxes, (v) thickeners, (vi) film formers, (vii) preservatives, and (viii) perfumes.

Emollients

Emollients may be used according to the invention in amounts which are effective to prevent or relieve dryness. Useful emollients include, without limitation: hydrocarbon oils and waxes; silicone oils; triglyceride esters; acetoglyceride esters; ethoxylated glyceride; alkyl esters; aleyl esters; fatty acids; fatty alcohols; fatty alcohol ethers; etheresters; lanolin and derivatives; polyhydric alcohols tolyols) and polyether derivatives; polyhydric alcohol polyol) esters; wax esters; beeswax derivatives; vegetable waxes; phospholipids; sterols; and amides.

Thus, for example, typical emollients include mineral oil, especially mineral oils having a viscosity in the range of 50 to 500 SUS, lanolin oil, mink oil, coconut oil, cocoa butter, olive oil, almond oil, macadamia nut oil, aloa extract, jojoba oil, safflower oil, corn oil, liquid lanolin, cottonseed oil, peanut oil, purceliin oil, perhydrosqualene (squalene), caster oil, polybutene, odorless mineral spirits, sweet almond oil, avocado oil, calophyllum oil, ricin oil, vitamin E acetate, olive oil, mineral spirits, cetearyl alcohol (mixture of fatty alcohols consisting predominantly of cetyl and stearyl alcohols), linolenic alcohol, oleyl alcohol, octyl dodecanol, the oil of cereal germs such as the oil of wheat germ cetearyl octanoate (ester of cetearyl alcohol and 2-ethylhexanoic acid), cetyl palmitate, diisopropyl adipate, isopropyl palmitate, octyl palmitate, isopropyl myristate, butyl myristate, glyceryl stearate, hexadecyl stearate, isocetyl stearate, octyl stearate, octylhydroxy stearate, propylene glycol stearate, butyl stearate, decyl oleate, glyceryl oleate, acetyl glycerides, the octanoates and benzoates of (C12–C15) alcohols, the octanoates and decanoates of alcohols and polyalcohols such as those of glycol and glycerol, and ricin-oleates of alcohols and poly alcohols such as those of isopropyl adipate, hexyl laurate, octyl dodecanoate, dimethicone copolyol, dimethiconol, lanolin, lanolin alcohol, lanolin wax, hydrogenated lanolin, hydroxylated lanolin, acetylated lanolin, petrolatum, isopropyl lanolate, cetyl myristate, glyceryl myristate, myristyl myristate, myristyl lactate, cetyl alcohol, isostearyl alcohol stearyl alcohol, and isocetyl lanolate, and the like.

Emulsifiers

Emulsifiers (i.e., emulsifying agents) are also used in certain aspects of the invention in amounts effective to provide uniform blending of ingredients of the composition. Useful emulsifiers include (i) anionics such as fatty acid soaps, e.g., potassium stearate, sodium stearate, ammonium stearate, and triethanolamine stearate; polyol fatty acid monoesters containing fatty acid soaps, e.g., glycerol monostearate containing either potassium or sodium salt; sulfuric esters (sodium salts), e.g., sodium lauryl 5 sulfate, and sodium cetyl sulfate; and polyol fatty add monoesters containing sulfuric esters, e.g., glyceryl monostearate containing sodium lauryl sulfate; (ii) cationics chloride such as N(stearoyl colamino formylmethyl) pyridium; N-soya-N-ethyl morpholinium ethosulfate; alkyl dimethyl benzyl ammonium chloride; diisobutylphenoxytheoxyethyl dimethyl benzyl ammonium chloride; and cetyl pyridium chloride; and (iii) nonionics such as polyoxyethylene fatty alcohol ethers, e.g., monostearate; polyoxyethylene lauryl alcohol; polyoxypropylene fatty alcohol ethers, e.g., propoxylated oleyl alcohol; polyoxyethylene fatty acid esters, e.g., polyoxyethylene stearate; polyoxyethylene sorbitan fatty acid esters, e.g., polyoxyethylene sorbitan monostearate; sorbitan fatty acid esters, e.g., sorbitan; polyoxyethylene glycol fatty acid esters, e.g., polyoxyethylene glycol monostearate; and polyol fatty acid esters, e.g., glyceryl monostearate and propylene glycol monostearate; and. ethoxylated lanolin derivatives, e.g., ethoxylated lanolins, ethoxylated lanolin alcohols and ethoxylated cholesterol.

Surfactants

Surfactants are also used in certain compositions of the invention. Suitable surfactants may include, for example, those surfactants generally grouped as cleansing agents, emulsifying agents, foam boosters, hydrotropes, solubilizing agents, suspending agents and nonsurfactants (facilitates the dispersion of solids in liquids).

The surfactants are usually classified as amphoteric, anionic, cationic and nonionic surfactants. Amphoteric surfactants include acylamino acids and derivatives and N-alkylamino acids. Anionic surfactants include: acylamino adds and salts, such as, acylglutamates, acylpeptides, acylsarcosinates, and acyltaurates; carboxylic acids and salts, such as, alkanoic acids, ester carboxylic acids, and ether carboxylic acids; sulfonic acids and salts, such as, acyl isethionates, alkylaryl sulfonates, alkyl sulfonates, and sulfosuccinates; sulfuric acid esters, such as, alkyl ether sulfates and alkyl sulfates. Cationic surfactants include: alkylamines, alkyl imidazolines, ethoxylated amines, and quaternaries (such as, alkylbenzyldimethylammonium salts, alkyl betaines, heterocyclic ammonium salts, and tetra alkylammonium salts). And nonionic surfactants include: alcohols, such as primary alcohols containing 8 to 18 carbon atoms; alkanolamides such as alkanolamine derived amides and ethoxylated amides; amine oxides; esters such as ethoxylated carboxylic acids, ethoxylated glycerides, glycol esters and derivatives, monoglycerides, polyglyceryl, esters, polyhydric alcohol esters and ethers, sorbitan/sorbitol esters, and triesters of phosphoric acid; and ethers such as ethoxylated alcohols, ethoxylated lanolin, ethoxylated polysiloxanes, and propoxylated polyoxyethylene ethers.

Waxes

Suitable waxes which are useful in accord with the invention include: animal waxes, such as beeswax, spermaceti, or wool wax (lanolin); plant waxes, such as carnauba or candelilla; mineral waxes, such as montan wax or ozokerite; and petroleum waxes, such as paraffin wax and microcrystalline wax (a high molecular weight petroleum wax). Animal, plant, and some mineral waxes are primarily esters of a high molecular weight fatty alcohol with a high molecular weight fatty acid. For example, the hexadecanoic acid ester of tricontanol is commonly reported to be a major component of beeswax.

Other suitable waxes according to the invention include the synthetic waxes including polyethylene polyoxyethylene and hydrocarbon waxes derived from carbon monoxide and hydrogen.

Representative waxes also include: ceresin; cetyl esters; hydrogenated jojoba oil; hydrogenated jojoba wax; hydrogenated rice bran wax; Japan wax; jojoba butter; jojoba oil; jojoba wax; munk wax; montan acid wax; ouricury wax; rice bran wax; shellac wax; sufurized jojoba oil; synthetic beeswax; synthetic jojoba oils; trihydroxystearin; cetyl alcohol; stearyl alcohol; cocoa butter; fatty acids of lanolin; mono-, di- and 25 triglycerides which are solid at 25° C., e.g., glyceyl tribehenate (a triester of behenic acid and glycerine) and C1g-C36 acid triglyceride (a mixture of triesters of C1g-C36 carboxylic acids and glycerine) available from Croda, Inc., New York, N.Y. under the tradenames Syncrowax HRC and Syncrowax HGL-C, respectively; fatty esters which are solid at 25° C.; silicone waxes such as methyloctadecaneoxypolysiloxane and poly (dimethylsiloxy) stearoxysiloxane; stearyl mono- and diethanolamide; rosin and its derivatives such as the abietates of glycol and glycerol; hydrogenated oils solid at 25° C.; and sucroglycerides. Thickeners (viscosity control agents) which may be used in effective amounts in aqueous systems include: algin; carbomers such as carbomer 934, 934P, 940 and 941; cellulose gum; cetearyl alcohol, cocamide DEA, dsxtrin; gelatin; hydroxyethylcellulose; hydroxypropylcellulose; hydroxypropyl methylcelulose; magnesium aluminum silicate; myristyl alcohol; oat flour; oleamide DEA; oleyl alcohol; PEG-7M,; PEG14M; PEG9OM; stearamide DEA; Stearamide MEA; stearyl alcohol; tragacanth gum; wheat starch; xanthan gum; and the like in the above list of thickeners, DEA is diethanolamine, and MEA is monoehanolamine. Thickeners (viscosity control agents) which may be used in effective amounts in nonaqueous systems include, aluminum stearates; beeswax; candelila wax; camauba; ceresin; cetearyl alcohol; cetyl alcohol; cholesterol; hydrated silica; hydrogenated castor oil; hydrogenated cottonseed oil; hydrogenated soybean oil; hydrogenated tallow glyceride; hydrogenated vegetable oil; hydroxypropyl cellulose; lanolin alcohol; myristyl alcohol; octytdodecyl stearoyl sulfate; oleyl alcohol; ozokerite; microcystalline wax; paraffin; pentaerythrityl tetraoctanoate; polyacrylamide; polybutene; polyethylene; propylene glycol dicaprylate; propylene glycol dipelargonate; stearalkonium hectorite; stearyl alcohol; stearyl stearate; synthetic beeswax; trihydroxystearin; trilinolein; tristearin; zinc stearate; and the like.

Film Formers

Suitable film formers which are used in accord with the invention keep the composition smooth and even and include, without limitation: acrylamide/sodium acrylate copolymer; ammonium acrylates copolymer; Balsam Peru; cellulose gum; ethylene/maleic anhydride copolymer; hydroxyethylcellulose; hydroxypropylcellulose; polyacrylamide; polyethylene; polyvinyl alcohol; pvm/MA copolymer (polyvinyl methylether/maleic anhydride); PVP (polyvinylpyrrolidone); maleic anhydride copolymer such as PA-18 available from Gulf Science and Technology; PVP/hexadecene copolymer such as Ganex V-216 available from GAF Corporation; acryliclacrylate copolymer; and the like.

Generally, film formers can be used in amounts of about 0.1% to about 10% by weight of the total composition with about 1% to about 8% being preferred and about 0.10/O to about 5% being most preferred. Humectants can also be used in effective amounts, including: fructose; glucose; glulamic acid; glycerin; honey; maltitol; methyl gluceth-10; methyl gluceth-20; propylene glycol; sodium lactate; sucrose; and the like.

Preservatives

Preservatives according to certain compositions of the invention include, without limitation: butylparaben; ethylparaben; imidazolidinyl urea; methylparaben; O-phenylphenol; propylparaben; quaternium-14; quaternium-15; sodium dehydroacetate; zinc pyrithione; and the like.

The preservatives are used in amounts effective to prevent or retard microbial growth. Generally, the preservatives are used in amounts of about 0.1% to about 1% by weight of the total composition with about 0.1% to about 0.8% being preferred and about 0.1% to about 0.5% being most preferred.

Perfumes

Perfumes (fragrance components) and colorants (coloring agents) well known to those skilled in the art may be used in effective amounts to impart the desired fragrance and color to the compositions of the invention.

Other ingredients which can be added or used in amounts effective for their intended use, including: biological additives to enhance performance or consumer appeal such as amino acids, proteins, vanilla, aloe extract, bioflavinoids, and the like; buffering agents, chelating agents such as EDTA; emulsion stabilizers; pH adjusters; opacifying agents; and propellants such as butane carbon dioxide, ethane, hydrochlorofluorocarbons 22 and 142b, hydrofluorocarbon 152a, isobutane, isopentane, nitrogen, nitrous oxide, pentane, propane, and the like.

The ingredients described above -sunscreening agents, emollients, emulsifiers, surfactants, solvents for sunscreening agents, waxes, thickeners, film formers, humectants, preservatives, surfactants, perfumes, coloring agents, biological additives, buffering agents, chelating agents, emulsion stabilizers, opacifying agents, pH adjusters, and propellants- are well known to those skilled in the art. The determination of which ingredients to use to obtain the intended formulations, and the determination of the amounts which may be used to achieve the intended functions and effects of these ingredients are well within the capabilities of those skilled in the art without the need for undue experimentation. Further information may be obtained on these ingredients, for example, by reference to: Cosmetics & Toiletries, Vol. 102, No. 3, March 1987; Balsam, M. S., et al., editors, Cosmetics Science and Technology, 2nd edition, Vol. 1, pp 27–104 and 179–222 Wiley-Interscience, New York, 1972; Cosmetics & Toiletries, Vol. 104, pp 67–111, February 1989; Cosmetics & Toiletries, Vol. 103, No. 12, pp 100–129, December 1988; Nikitakis, J. M., editor, CTFA Cosmetic Ingredient Handbrook, First Edition, published by The Cosmetic, Toiletry and Fragrance Association, Inc., Washington, D.C., 1988; Muldtar, H, editor, Pharmacology of the Skin, CRC Press 1992; and Green; F J, The Sigma-Aldrich Handbook of Stains, Dyes and Indicators., Aldrich Chemical Company, Milwaukee Wis., 1991.

A representative lotion formulation is listed below in Table 1, which is broken into three parts.

TABLE 1

TYPICAL LOTION FORMULA

Part 1

| | |
|---|---|
| lanolin | 0.2–1% |
| cocoa butter | 2.0–5% |
| emcol RHT (glycelyl slearate)[1] | 2.0–4% |
| hystren~5016 (stearic acid)[2] | 2.0–4% |
| vitamin E acetate | 0.1–0.5% |
| aloe vera lipo quinone extract | 0.1–1.0% |
| jojoba o | 0.1–1.0% |
| mineral oil | 1.0–7% |
| propylparaben | 0.1–1% |
| medical fluid 360 (dimethicone)[3] | 0.1–1% |

Part 2

| | |
|---|---|
| water | 40–60% |
| carbopol 941 (1%) (polyacrylic acid polymer)[4] | 10–35% |
| propylene glycol | 2.0–7% |
| triethanolamine 99% | 0.1–3% |
| lanogel 41 (PEG-75 lanolin)[5] | 0.25–1% |
| methylparaben | 0.1–0.5% |
| sequestrene Na2 | 0.01–0.08% |

Part 3

| | |
|---|---|
| perfume | 0.01–.5% |

Footnotes
[1]Witco Corp., Organics Division, NY, NY (also Witconol RHT)
[2]Humko Chemcal, Memphis, Tenn.
[3]Dow Corning Corp., Midland, Michigan
[4]B.F. Goodrich Specially Polymers and Chemical Division, Cleveland, Ohio
[5]Amerchol Corp., Edison, NJ To make the formulation listed in Table 1, parts 1 and 2 are heated separately to 180° F. Part 1 is then added to Part 2. The resultant blend is cooled to 120° F. and Part 3 is then added.

Other examples of formulations which are useful according to the invention include oil-in-water creams, oil-in-water lotions, water-in-oil lotions, oil-in-water resistant creams and lotions, sticks, gels, oils and mousses. Such formulations are found, for example, in Cosmetics & Toiletries, Vol. 102, pp 117–130, March 1987, the disclosure of which is incorporated herein by reference.

Still other examples of formulations which are useful according to the invention include hand and body lotions, oil-in-water emollient creams, moisturizing lotions, after sun emollient stick, facial spray mist, skin mousse and moisturizing gel. Such formulations are found, for example, in Cosmetics & Toiletries, Vol. 102, pp 47–160, April 1987, the disclosure of which is incorporated herein by reference.

Those skilled in the art will appreciate that the formulations described in the above cited Cosmetics & Toiletries references (March and April 1987) represent types of formulations which may be suitably modified to allow for the addition of color indicators, and that such modifications may be accomplished without the need for undue experimentation.

The CIs according to the invention include several distinct compounds, including the following:

PHENOLPHTHALEIN 3,3-Bis(4hydroxyphenyl)-1(3H0-isobenzofuranone.3.3Bis (4-hydroxyphenyl)phthalide

| | |
|---|---|
| Mol. Form.: | $C_{20}H_{14}O_4$ |
| F.W.: | 318.33 |
| Appearance: | White powder |
| Solubility: | H2O  1mg/ml |
| | EGME  100mg/ml |
| | ETOH  30mg/ml |

Phenolphthalein, 3,3-Bis(4-hydroxyphenyl)-1(3H0-isobenzofuranone. 3.3Bis (4-hydroxyphenyl)phthalide, a preferred acid-base indicator according to the invention, is made by condensing one mole of phthalic anhydride with two moles of phenol. The condensation product is usually isolated as the colorless lactone form. The disodium salt form is red due to the opening of the lactone rine and the concomitant paraquinoid-chromophore formation. However, with the addition of enough sodium hydroxide to form the trisodium carbinol salt, it becomes colorless again due to the elimination of the paraquinoidal structure.

α-CRESOLPHTHALEIN: 3,3-Dimethylphenolphthalein

| | |
|---|---|
| Mol. Form.: | $C_{22}H_{18}O_4$ |
| F.W: | 346.38 |
| Appearance: | Beige powder |
| Solubility: | H2O  1mg/ml |
| | EGME  90mg/ml |
| | ETOH  50mg/ml |

σ-Cresolphthalein, 3,3 Dimethylphenolphthalein, is a member of the phthalein-indicator series and is made by condensing one mole of phthalic anhydride with two moles of s-resol. This white, crystalline-powder product is soluable in alcohol and aqueous alkali solutions and very slightly soluable in water. An acid-base indicator, it has a visual-transition interval extending from pH 82(colorless) to pH 9.8 (red) and a pK of 9.4.

THYMOLPHTHALEIN

| | |
|---|---|
| Mol. Formula: | $C_{28}H_{30}O_4$ |
| F.W.: | 430.54 |
| Appearance: | White powder |
| Solubility: | H2O  1mg/ml |
| | EGME  100mg/ml |
| | ETOH  70mg/ml |

Thymolphthalein is a hydroxytriarylmethane indicator that is made by condensing two moles of thymol with one mole of phthalic anhydride in the presence of heat and a condensing agent, such as stannin chloride. It is soluble in the lower aliphatic alcohols, acetone and dilute alkalies. It has a visual-transition interval of pH 8.8 (colorless) to pH 10.5 (blue).

Fluorescent Indicator
COUMARIN

| Mol. Formula: | $C_9H_6O_2$ |
| --- | --- |
| F.W.: | 146.15 |
| Appearance: | White crystalline powder |
| Solubility: | H2O <0.1mg/ml |
| | EGME <0.1mg/ml |
| | ETHOL <0.1mg/ml |

Coumarin is used as a fluorescent indicator displaying a fluorecent-transition interval of pH 8.0 (colorless) to pH 9.5 (green).

Other fluorescent indicators according to the invention include: (1) 2,3, dioxyxanthone with a transition interval pH 5.4 (colorless) to pH 7.6 blue/violet; and (ii) coumeric acid with a transition interval pH 7.2 (colorless) to pH 7.5 (blue).

Other nonfluorecent indicators according to the invention include: (i) 6.8-dinitro-2,4-(1H) quinazolinedione with a transition interval pH 6.4 (colorless) to pH 8.0 (yellow); and (ii) ethyl-bis (2,4-dimethylphenyl) ethanoate with a transition interval pH 8.4 (colorless) to pH 9.6 (Blue).

FIG. 1 illustrates a typical use of the invention. Specifically, FIG. 1 shows a human arm 10 with a visible and evenly distributed application of sunscreen lotion 12, constructed according to the invention, applied to a section 14 of the arm 10. The section 14 is visible because of the pH indicator described herein. FIG. 1 also shows the same arm 10' after a short time period—e.g., between about 0.5 and 10 minutes, and preferably about one minute—and wherein the arm 10' is substantially the normal color of human skin.

Figure 2:
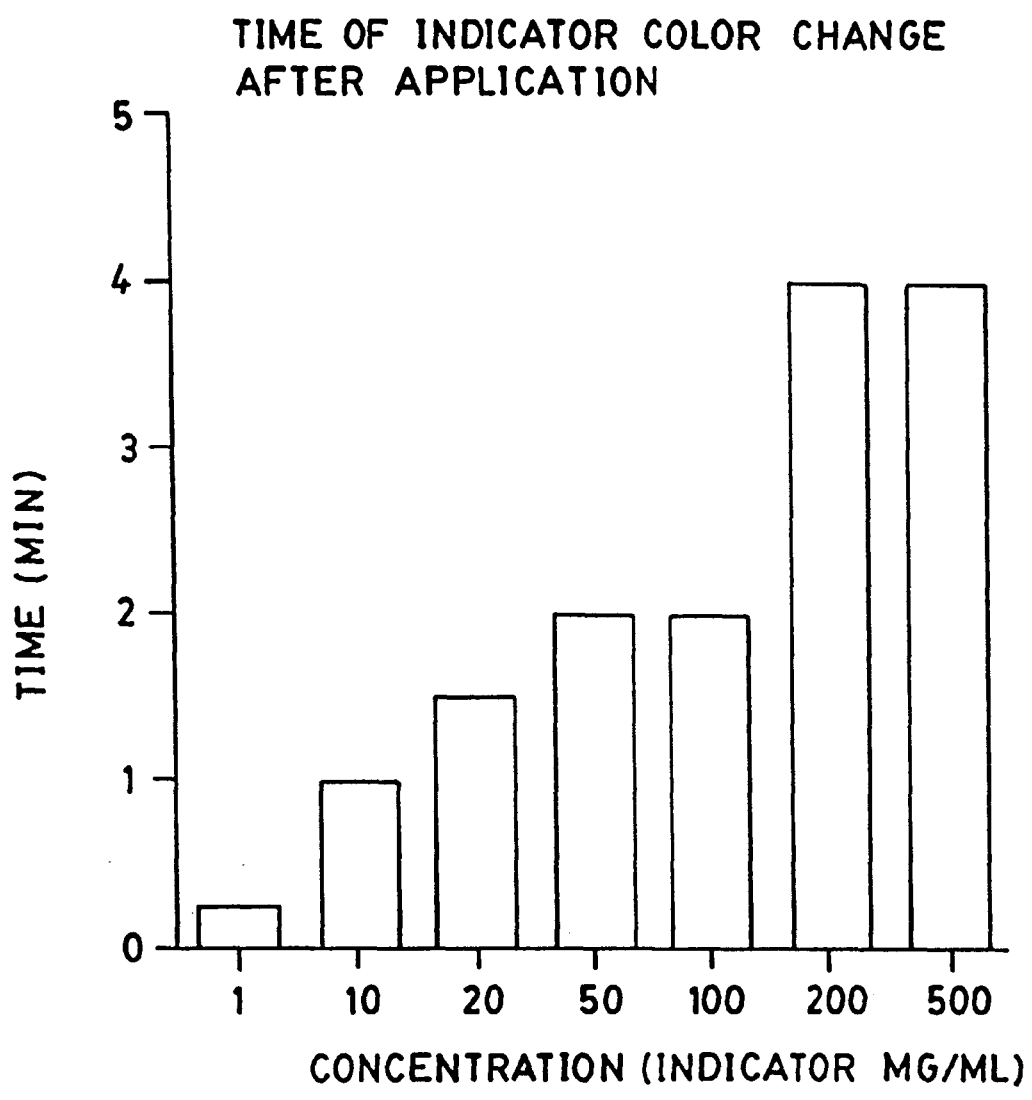
FIG. 2 is a graph illustrating certain effects of indicator concentrations on the time course of CI change from visible to clear.

FIG. 2 shows a graph illustrating the effects of indicator concentration on the time course of CI change from visible to clear. Specifically, a phenolphthalein color indicator was dissolved in phosphate buffered saline at the indicated concentration and applied to a subjects skin. The time from application to the complete change in color was measured and recorded. The bars indicate the mean time of three trials.

Figure 3:
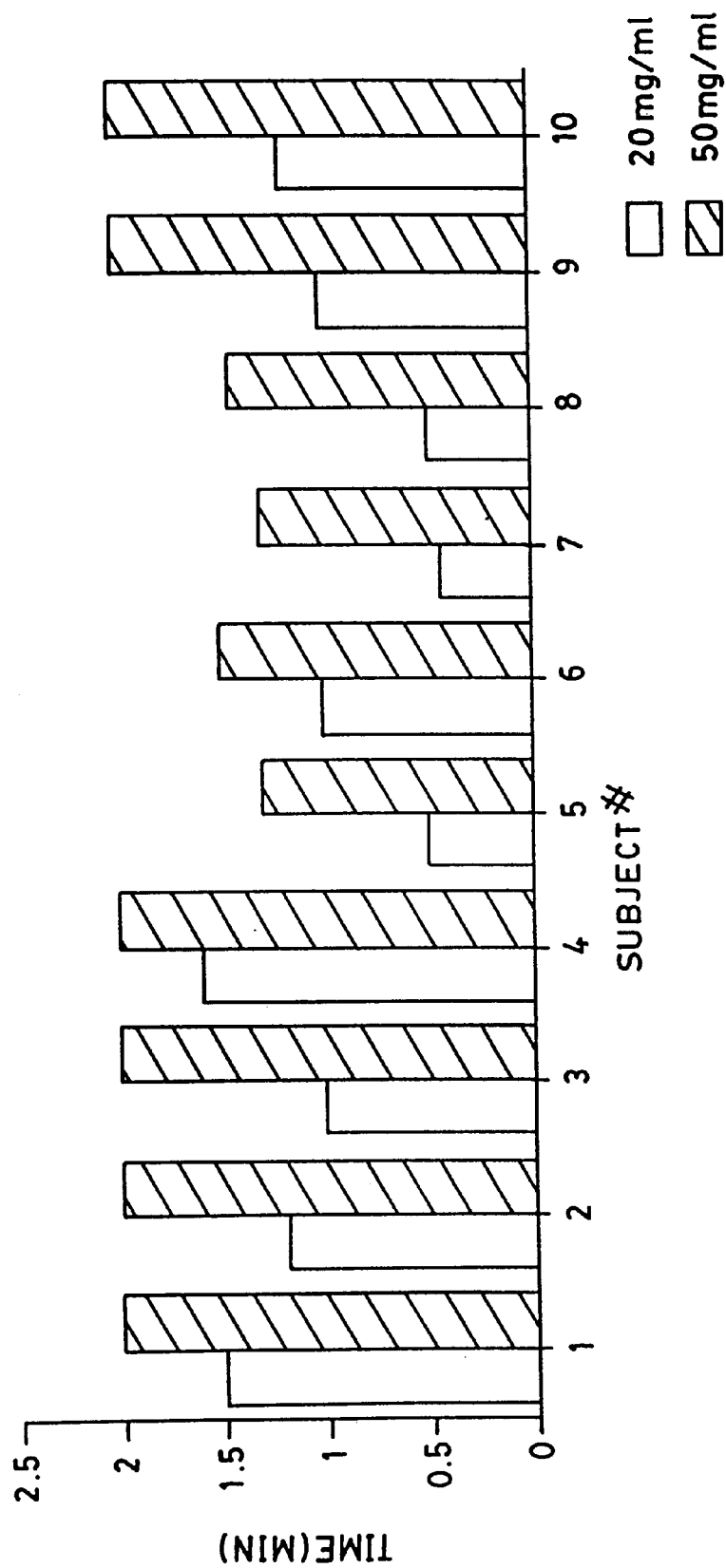
FIG. 3 is a graph illustrating certain effects of concentrations on CI change from visible to clear when dissolved in a common sunscreen in ten volunteers.

FIG. 3 shows a graph illustrating the effect of concentration on a CI change from visible to clear when dissolved in a common sunscreen in ten volunteers. The concentrations were 20 and 50 mg/ml. Specifically, in FIG. 3, the time of color change (on the vertical axis) at two concentrations of phenolthalien dissolved in a common sunscreen was measured on the forearms of ten separate volunteers. Variability was expected and observed. A concentration of 50 mg/ml provided the most consistant results of the indicator changing from visible to colorless in 1–2 minutes.

Figure 4:
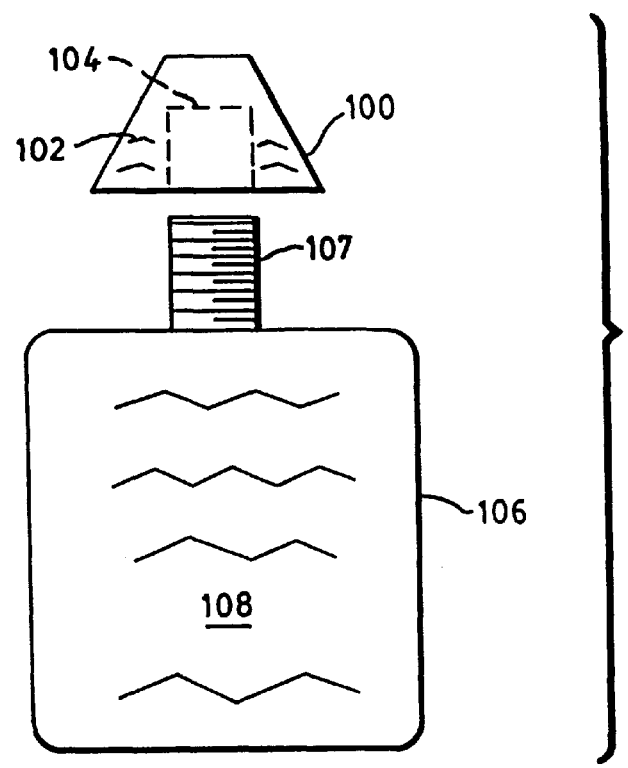
FIG. 4 shows a cap constructed according to the invention for adding a CI selectively to a lotion suitable for application on the body.

FIG. 4 is a diagrammatic representation of an apparatus according to the invention. Specifically, FIG. 4 shows a cap 100 constructed according to the invention. The cap 100 contains a color indicator 102 and includes a threading portion 104 (illustrated as an outline because the threads are internal to the illustrated view) which can attach, via a threading or screw action, onto a lotion container 106 (specifically onto the top threads 107). The lotion container 106 is of the prior art type known to the public for containing lotions, creams, gels, mousses, sunscreen agents, and the like (collectively, the "lotion 108"). The invention colors the lotion 108 upon use by a user desirous of applying the lotion 108 to the user's skin by mixing the color indicator 102 with the lotion 108 during application Accordingly, the lotion 108 appears colored upon application, but typically becomes colorless after a period of time on the user's skin (depending upon the intended color of the lotion 108).

Figure 4A:
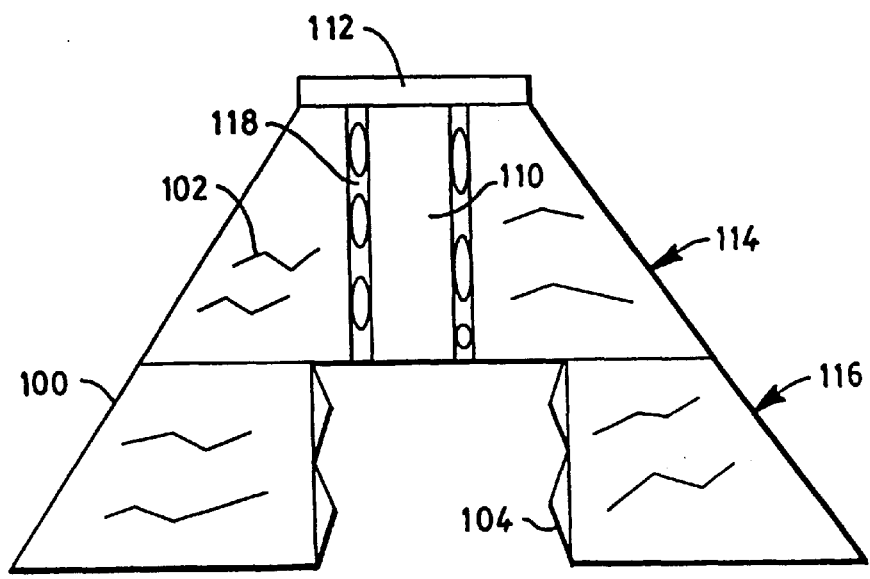
FIG. 4A illustrated further features of the cap of FIG. 4.

FIG. 4A illustrates further features of the cap 100. Specifically, FIG. 4A shows a cutaway side view of the cap 100 with threading portion 104 used to attach the cap 100 to a container, e.g., the container 106 of FIG. 4. A conduit 110 provides a path for the lotion to pass through the cap 100 to the user's skin, while a top seal 112 selectively seals the cap 100, and hence the lotion, so that the lotion 108 is safely sealed while not in use. Such a cap is known to those skilled in the art.

Figure 4B:
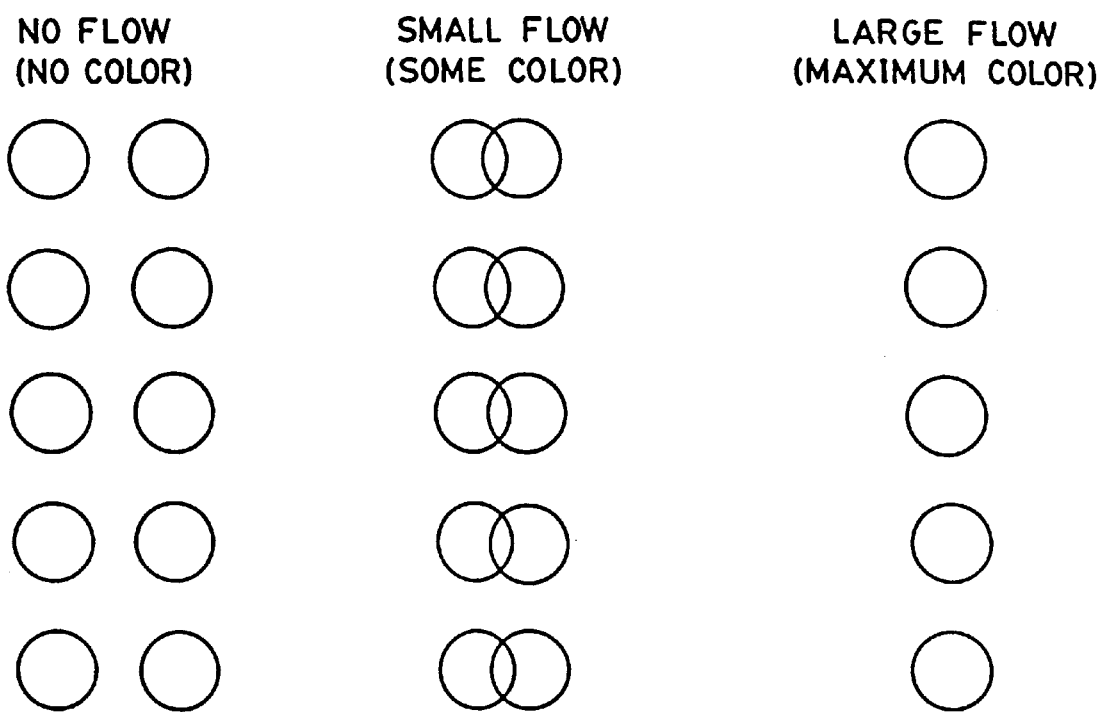
FIG. 4B illustrates flow rate overlapping holes which are suitable for use with the cap of FIG. 4 to control flow and color rate.

FIG. 4A also illustrates a twist portion 114 which provides a user with a mechanism to control the flow of color indicator to the conduit 110. A user selectively twists the top portion 114 while keeping the lower portion 116 still to adjust the overlapping flow holes 118. These flow holes 118, shown in FIG. 4B, provide varying flow diameters between the cavity 120, containing the color indicator 102, and the conduit 110. Accordingly, a user can adjust the amount of color added to the lotion upon application, from No Flow (i.e., no color), to Small Flow (i.e, some color), to Large Flow (i.e., maximum color), such as illustrated in FIG. 4B.

It is accordingly intended that all matter contained in the above description or shown in the accompanying drawings be interpreted as illustrative rather than in a limiting sense.

It is also intended that the following claims cover all of the generic and specific features of the invention as described herein, and all statements of the scope of the invention which, as a matter of language, might be said to fall there between.

Having described the invention, what is claimed as new and secured by Letters Patent is:

1. A composition for application to human skin, comprising a formulation and a physiologically compatible color indicator, the color indicator being mixed with the formulation to form a mixture that has a non-white, visible color when applied to the skin, and that has substantially no color when distributed evenly over the skin.

2. A composition according to claim 1, wherein the color indicator is selected from the group consisting essentially of a pH indicator and a coloring agent.

3. A composition according to claim 2, wherein the coloring agent comprises a colorant which imparts a selected color to the formulation.

4. A composition according to claim 2, wherein the pH indicator is selected from the group consisting essentially of phenolphthalein, σ-cresolphthalein, thymolphthalein, quinazolinedione, ethyl-bis ethanoate, coumarin, dioxyxanthone, and 6.8-dinitro-2,4-(1H) quinazolinedione.

5. A composition according to claim 2, wherein the pH indicator has substantially no visible color within a pH range of the skin, and which has a visible color outside the pH range, wherein the mixture turns substantially colorless after prolonged contact with the skin.

6. A composition according to claim 1, wherein the formulation forms one of a lotion, gel, mousse, medication, cream, moisturizer, ointment, waxed base stick, aerosol, alcohol stick, oil, and mist for facilitating application to the skin.

7. A composition according to claim 1, wherein the color indicator comprises means for imparting a red color.

8. A composition according to claim 1, wherein the color indicator comprises means for imparting a fluorescent color.

9. A composition according to claim 1, wherein the formulation comprises a sunscreen.

10. A composition according to claim 1, wherein the formulation comprises a sunscreening agent.

11. A composition according to claim 10, wherein the agent comprises one of UVA type sunscreen agent and UVB type sunscreen agent.

12. A composition according to claim 10, wherein the agent comprises a physical sunscreening agent.

13. A composition according to claim 1, wherein the color indicator comprises means for imparting a blue color.

14. A composition according to claim 1, wherein the color indicator comprises means for imparting a violet color.

15. A composition according to claim 1, wherein the color indicator comprises means for imparting a yellow color.

16. A method of forming a formulation suitable for application to human skin, the formulation of the type comprising one of a lotion, gel, mousse, medication, cream, moisturizer, ointment, waxed base stick, aerosol, alcohol stick, oil, and mist, comprising the steps of providing a physiologically compatible color indicator, and mixing the formulation with the color indicator so as to colorize the formulation for application to human skin.

17. A method according to claim 16, wherein the step of providing a color indicator comprises the further improvement of providing a pH indicator which has visible color outside a pH range of the skin and which has substantially no visible color at the pH of the skin.

18. A method according to claim 16, wherein the step of providing a color indicator comprises the further improvement of providing a colorant to selectively add color to the formulation wherein the formulation has visible color when applied to the skin.

19. A method according to claim 16, wherein the step of providing a color indicator comprises the further step of selecting a colorant from the group of yellow, red, blue, violet and fluorescent, whereby the colorant imparts a non-white visible color when applied to the skin.

20. A method of applying a colored formulation to human skin, comprising the steps of mixing a physiological color indicator with a sunscreen, the color indicator imparting a non-white visible color when mixed with the sunscreen, and applying the mixture of the color indicator and the sunscreen to the skin, thereby visibly indicating regions of the skin protected with the sunscreen.

21. A method according to claim 20, further comprising the step of providing a sunscreen that is selected from the group of lotions, gels, mousses, creams, moisturizers, ointments, aerosols, oils, and mists.

22. A method according to claim 20, further comprising the step of selecting a color indicator to impart a fluorescent visible color when applied to the skin.

23. A method according to claim 20, further comprising the step of selecting a color indicator to impart a visible color selected from the group of blue, red, yellow and violet.

24. A moisturizing composition for application to human skin, comprising a lotion and a physiologically compatible color indicator, the color indicator being mixed with the lotion to form the composition that has a non-white, visible color when applied to the skin, and that has substantially no color when distributed evenly over the skin.

\* \* \* \* \*

UNITED STATES PATENT AND TRADEMARK OFFICE
CERTIFICATE OF CORRECTION

PATENT NO : 5,955,062
DATED : September 21, 1999
INVENTOR(S) : John McEleney et al.

It is certified that error appears in the above-identified patent and that said Letters Patent is hereby corrected as shown below:

On title page, item 73 Assignee
replace "SeeUV, Charlestown, Mass."
with --IPA, LLC, A Texas Limited Liability Company, Ft. Worth, TX --.

Signed and Sealed this

Twenty-second Day of August, 2000

*Attest:*

Q. TODD DICKINSON

*Attesting Officer*   *Director of Patents and Trademarks*